(12) United States Patent
Teuber et al.

(10) Patent No.: US 6,878,701 B2
(45) Date of Patent: Apr. 12, 2005

(54) POTASSIUM CHANNEL BLOCKING AGENTS

(75) Inventors: Lene Teuber, Vaerlose (DK); Soren Peter Olesen, Klampenborg (DK); Dorte Strobaek, Farum (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 10/029,168

(22) Filed: Dec. 28, 2001

(65) Prior Publication Data

US 2002/0128279 A1 Sep. 12, 2002

Related U.S. Application Data

(63) Continuation of application No. PCT/DK00/00332, filed on Jun. 22, 2000.

(30) Foreign Application Priority Data

Jun. 29, 1999 (DK) .......................................... 1999 00927

(51) Int. Cl.⁷ .................... C07D 487/18; C07D 487/22; A61K 31/529; A61K 31/4188
(52) U.S. Cl. ........................ 514/183; 514/257; 540/472
(58) Field of Search ................................. 514/183, 257; 540/472

(56) References Cited

U.S. PATENT DOCUMENTS

| 5,739,127 A | 4/1998 | Schohe-Loop et al. ..... 514/218 |
| 5,760,230 A | 6/1998 | Schohe-Loop et al. ..... 544/284 |
| 5,874,438 A | 2/1999 | Schohe-Loop et al. ..... 514/260 |

FOREIGN PATENT DOCUMENTS

| WO | 97/48705 A1 | 12/1997 |
| WO | 00/01676 A1 | 1/2000 |

OTHER PUBLICATIONS

STN International, Soichi et al., Mem. Inst. Sci. Ind. Res., Osaka Univ. No. 1986:109563, Document No. 104:104653, (1985), pp. 53–67.

STN International, Mikhailov, A. S. et al., Zh. Obshch. Khim., No. 1996:605017, Document No. 126:31340, (1996), two pages (1 & 2).

STN International, Mikhailov, A. S. et al., Dokl. Akad. Nauk, No. 1999:630451, Document No. 131:351293, (1998), p. 1–A & p. 2–A.

Dimitrios Galanakis et al., J. Med. Chem., vol. 38, 1995 pp. 595–606.

*Primary Examiner*—Bruck Kifle
(74) *Attorney, Agent, or Firm*—Birch, Stewart, Kolasch & Birch, LLP

(57) ABSTRACT

Compounds of Formula I:

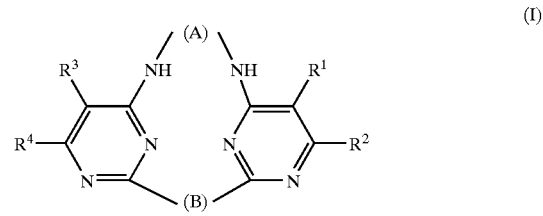

wherein A and B are linking groups; $R^1$, $R^2$, $R^3$ and $R^4$ are defined moieties. An exemplary compound is:

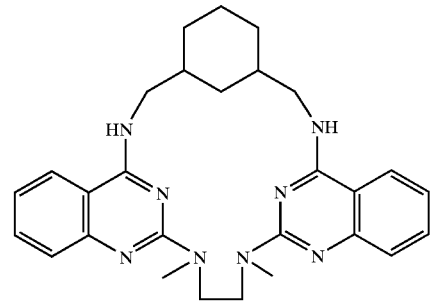

These compounds function as potassium channel blocking agents, and can be used in a wide variety of pharmaceutical compositions for the treatment of a wide variety of diseases.

4 Claims, No Drawings

POTASSIUM CHANNEL BLOCKING AGENTS

This application is a Continuation of copending PCT International Application No. PCT/DK00/00332 filed on Jun. 22, 2000, which was published in English and which designated the United States, and on which priority is claimed under 35 U.S.C. §120, the entire contents of which are hereby incorporated by reference.

TECHNICAL FIELD

This invention relates to novel potassium channel blocking agents, and their use in the preparation of pharmaceutical compositions.

Moreover the invention is directed to pharmaceutical compositions useful for the treatment or alleviation of diseases or disorders associated with the activity of potassium channels, in particular asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

A number of neuromuscular blocking agents with effect on SK channels exist, e.g. apamin, atracurium, pancuronium and tubocurarine.

WO 97/48705 discloses a particular group of chemical compounds useful as calcium activated potassium channel blocking agents. However, their selectivity in respect of the SK channel is not disclosed.

U.S. Pat. Nos. 5,739,127 and 5,760,230 disclose another group of 4.4'-bridged bis-2,4-diaminoquinazoline derivatives acting on potassium channels.

SUMMARY OF THE INVENTION

The present invention resides in the provision of novel chemical compounds capable of selectively blocking SK channels, or subtypes of SK channels.

Moreover the invention is directed to pharmaceutical compositions useful for the treatment or alleviation of diseases or disorders associated with the activity of potassium channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

Accordingly, in its first aspect, the invention provides novel chemical compounds selected from the group represented by the general Formulas I to IV, below.

In another aspect, the invention provides pharmaceutical compositions comprising an effective amount of a chemical compound of the invention.

In further aspects the invention relates to the use of a chemical compound of the invention for the manufacture of a medicament for the treatment or alleviation of diseases or disorders associated with the activity of potassium channels, and to method of treatment or alleviation of disorders or conditions responsive to blockade of potassium channels.

DETAILED DISCLOSURE OF THE INVENTION
Potassium Channel Blocking Agents

In its first aspect, the invention provides novel cyclic bis-amino-quinazolines. The novel chemical compounds of the invention is particularly useful as potassium channel blocking agents.

Therefore, the invention provides a potassium channel blocking agent, in particular a SK channel blocking agent, selected from the group represented by the general Formulas I to IV, below.

Formula I

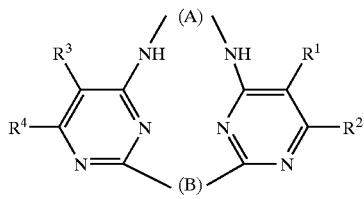

(I)

wherein

A and B, independently of each another, represent a linking group having a chain length comprising of from 1 to 20 separate bonds; and $R^1$, $R^2$, $R^3$ and $R^4$, independently of each another, represent hydrogen, halogen, alkyl, alkenyl, alkynyl, cycloalkyl, amino, trihalogenmethyl, nitro, cyano, or a group of the formula —OR', —SR', —R'OR", —R'SR", —C(O)R', —C(S)R', —C(O)OR', —C(S)OR', —C(O)SR', —C(S)SR', —C(O)NR'(OR"), —C(S)NR'(OR"), —C(O)NR'(SR"), —C(S)NR'(SR"), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', CH$_2$SR', or —SO$_2$NR'R";

a partially or completely saturated mono- or polycyclic carbocyclic group, a mono- or poly-cyclic heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR'; or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR'; or $R^1$ and $R^2$ together, and/or $R^3$ and $R^4$ together, form a partially or completely saturated mono- or polycyclic carbocyclic group, or a mono- or poly-cyclic heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR'; or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein R' and R", independently of each another, represent hydrogen, alkyl, alkenyl, alkynyl, cycloalkyl, alkoxy or alkoxyalkyl, or a group of the formula NR'''R'''', wherein R''' and R'''', independently of each another, represent hydrogen or an alkyl group.

In a preferred embodiment, A and B, independently of each another, represent a linear or branched alkylene chain having of from 1 to 15 carbon atoms, which alkylene group may be interrupted by one or more oxygen or sulphur atoms, or by one or more groups of the formula —NR'''—, or =NR''', wherein R''' represents hydrogen or alkyl; or a di-radical of the formula —(CH$_2$)$_a$—D—(CH$_2$)$_b$—, wherein a and b, which may be identical or different, represent the number 0, 1, 2, 3, 4 or 5, and D represents a cycloalkyl group, or an aryl group of from 6 to 12 carbon atoms, which aryl group may in particular be a phenyl group or a biphenyl group.

In a more preferred embodiment, A and B, independently of each another, represent decamethylene; octamethylene; hexamethylene; pentamethylene; tetramethylene; trimethylene; dimethylene; N,N'-dimethyl-diamino-methylene; N,N'-dimethyl-diamino-dimethylene; N,N'-dimethyl-diamino-trimethylene; (cis and/or trans)-1,5-cyclooctylene; (cis and/or trans)-1,3-dimethylcyclohexane-(α,α'-diyl; para-xylene-α,α'-diyl; meta-xylene-α,α'-diyl; 1,3-phenylene; biphenyl-3,3'-diyl; 4,4'-dimethyl-bibenzyl-α,α'-diyl; 4,4'-dimethyl-diphenylmethane-α,α'-diyl; 4,4'-dimethyl-cis/trans-stilbene-α,α'-diyl; 2,6-bis(4'-methyl-phenyl)pyridine-α,α'-diyl; 3,3'-dimethyl-biphenyl-α,α'-diyl; or 2,7-dimethyl-9H-fluorene-α,α'-diyl.

Formula II

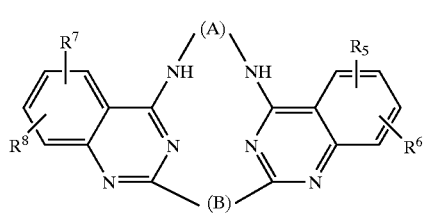

(II)

wherein

A and B, independently of each another, represent a linear or branched alkylene chain having of from 1 to 15 carbon atoms, which alkylene group may be interrupted by one or more oxygen or sulphur atoms, or by one or more groups of the formula —NR'''—, or =NR''', wherein R''' represents hydrogen or alkyl; or a di-radical of the formula —(CH$_2$)$_a$—D—(CH$_2$)$_b$—, wherein a and b, which may be identical or different, represent the number 0, 1, 2, 3, 4 or 5, and D represents a cycloalkyl group, or an aryl group of from 6 to 12 carbon atoms, which aryl group may in particular be a phenyl group or a biphenyl group; and $R^5$, $R^6$, $R^7$ and $R^8$, independently of each another, represent halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR'; or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein R' and R", independently of each another, represent hydrogen, alkyl, alkenyl, alkynyl, cycloalkyl, alkoxy or alkoxyalkyl, or a group of the formula NR'"R"", wherein R'" and R"", independently of each another, represent hydrogen or alkyl.

In a preferred embodiment, A and B, independently of each another, represent decamethylene; octamethylene; hexamethylene; pentamethylene; tetramethylene; trimethylene; dimethylene; N,N'-dimethyl-diamino-methylene; N,N'-dimethyl-diamino-dimethylene; N,N'-dimethyl-diamino-trimethylene; (cis and/or trans)-1,5-cyclooctylene; (cis and/or trans)-1,3-dimethylcyclohexane-α,α"-diyl; para-xylene-α,α'-diyl; meta-xylene-α,α'-diyl; 1,3-phenylene; biphenyl-3,3'-diyl; 4,4'-dimethyl-bibenzyl-α,α'-diyl; 4,4'-dimethyl-diphenylmethane-α,α'-diyl; 4,4'-dimethyl-cis/trans-stilbene-α,α'-diyl; 2,6-bis(4'-methyl-phenyl)pyridine-α,α'-diyl; 3,3'-dimethyl-biphenyl-α,α'-diyl; or 2,7-dimethyl-9H-fluorene-α,α'-diyl.

In a most preferred embodiment, the chemical compound of Formula II is 20,23-dimethyl-2,10,18,20,23,25,32,33-octaazahexacyclo [22.7.1.1$^{4.8}$.1$^{11,19}$.0$^{12,17}$.0$^{26.31}$] tetratriaconta-1(32),11, 13, 15, 17, 19(33),24,26,28,30-decaene.

Formula III

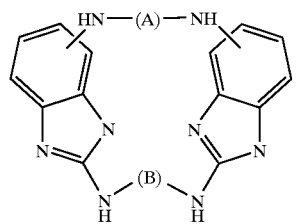

(III)

wherein

A and B, independently of each another, represent a linking group having a chain length comprising of from 1 to 20 separate bonds.

In a preferred embodiment, A and B, independently of each another, represent a linear or branched alkylene chain having of from 1 to 15 carbon atoms, which alkylene group may be interrupted by one or more oxygen or sulphur atoms, or by one or more groups of the formula —NR'"—, or =NR'", wherein R'" represents hydrogen or alkyl; or a di-radical of the formula —(CH$_2$)$_a$—D—(CH$_2$)$_b$—, wherein a and b, which may be identical or different, represent the number 0, 1, 2, 3, 4 or 5, and D represents a cycloalkyl group, or an aryl group of from 6 to 12 carbon atoms, which aryl group may in particular be a phenyl group or a biphenyl group.

In a more preferred embodiment, A and B, independently of each another, represent decamethylene; octamethylene; hexamethylene; pentamethylene; tetramethylene; trimethylene; dimethylene; N,N'-dimethyl-diamino-methylene; N,N'-dimethyl-diamino-dimethylene; N,N'-dimethyl-diamino-trimethylene; (cis and/or trans)-1,5-cyclooctylene; (cis and/or trans)-1,3-dimethylcyclohexane-α,α'-diyl; para-xylene-α,α'-diyl; meta-xylene-α,α'-diyl; 1,3-phenylene; biphenyl-3,3'-diyl; 4,4'-dimethyl-bibenzyl-α,α'-diyl; 4,4'-dimethyl-diphenylmethane-α,α'-diyl; 4,4'-dimethyl-cis/trans-stilbene-α,α'-diyl; 2,6-bis(4'-methyl-phenyl)pyridine-α,α'-diyl; 3,3'-dimethyl-biphenyl-α,α'-diyl; or 2,7-dimethyl-9H-fluorene-α,α'-diyl.

Formula IV

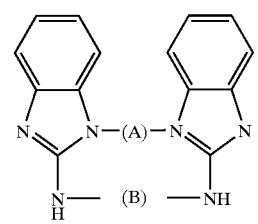

(IV)

wherein

A and B, independently of each another, represent a linking group having a chain length comprising of from 1 to 20 separate bonds.

In a preferred embodiment, A and B, independently of each another, represent a linear or branched alkylene chain having of from 1 to 15 carbon atoms, which alkylene group may be interrupted by one or more oxygen or sulphur atoms, or by one or more groups of the formula —NR'"—, or =NR'", wherein R'" represents hydrogen or alkyl; or a di-radical of the formula —(CH$_2$)$_a$—D—(CH$_2$)$_b$—, wherein a and b, which may be identical or different, represent the number 0, 1, 2, 3, 4 or 5, and D represents a cycloalkyl group, or an aryl group of from 6 to 12 carbon atoms, which aryl group may in particular be a phenyl group or a biphenyl group.

In a more preferred embodiment, A and B, independently of each another, represent decamethylene; octamethylene; hexamethylene; pentamethylene; tetramethylene; trimethylene; dimethylene; N,N'-dimethyl-diamino-methylene; N,N'-dimethyl-diamino-dimethylene; N,N'-dimethyl-diamino-trimethylene; (cis and/or trans)-1,5-cyclooctylene; (cis and/or trans)-1,3-dimethylcyclohexane-α,α'-diyl; para-xylene-α,α'-diyl; meta-xylene-α,α'-diyl; 1,3-phenylene; biphenyl-3,3'-diyl; 4,4'-dimethyl-bibenzyl-α,α'-diyl; 4,4'-dimethyl-diphenylmethane-α,α'-diyl; 4,4'-dimethyl-cis/trans-stilbene-α,α'-diyl; 2,6-bis(4'-methyl-phenyl)pyridine-α,α'-diyl; 3,3'-dimethyl-biphenyl-α,α'-diyl; or 2,7-dimethyl-9H-fluorene-α,α'-diyl.

Definition of Substituents

In the context of this invention a linking group designates a substituent that links the two parts of the molecule and to bring these parts into a relatively determined spatial interrelationship. The spacing group may also be termed a spacing group or a bridging group. The linking group of the invention should link the two parts of the molecule in a not too close and not too far distance from each another. It is currently believed that linking groups consisting of from 2 to 20 atoms, preferably carbon atoms, or carbon atoms interrupted by an oxygen or sulphur atom or by a group of the formula —NR—, wherein R represents hydrogen or alkyl, fulfil this requirement. Examples of such spacing groups are described herein, and summarised below.

| Spacing Group | Name |
|---|---|
| —(CH$_2$)$_{10}$— | decamethylene; |
| —(CH$_2$)$_8$— | octamethylene; |
| —(CH$_2$)$_6$— | hexamethylene; |
| —(CH$_2$)$_5$— | pentamethylene; |
| —(CH$_2$)$_4$— | tetramethylene; |
| —(CH$_2$)$_3$— | trimethylene; |
| —(CH$_2$)$_2$— | dimethylene; |
| —N(CH$_3$)—CH$_2$—N(CH$_3$)— | N,N'-dimethyl-diamino-methylene; |
| —N(CH$_3$)—CH$_2$—CH$_2$—N(CH$_3$)— | N,N'-dimethyl-diamino-dimethylene; |
| —N(CH$_3$)—CH$_2$—CH$_2$—CH$_2$—N(CH$_3$)— | N,N'-dimethyl-diamino-trimethylene; |
| 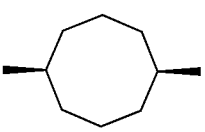 | (cis and/or trans)-1,5-cyclooctylene; |
| 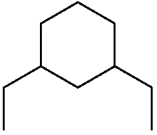 | (cis and/or trans)-1,3-dimethylcyclohexane-α,α'-diyl; |
| 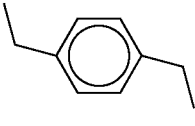 | para-xylene-α-α'-diyl; |
| 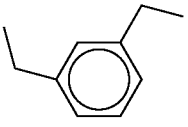 | meta-xylene-α,α'-diyl; |
| 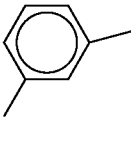 | 1,3-phenylene; |
| 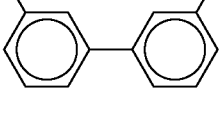 | biphenyl-3,3'-diyl; |
| 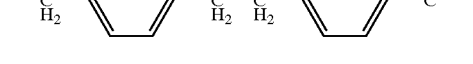 | 4,4'-dimethyl-bibenzyl-α,α'-diyl; |
| 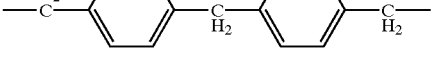 | 4,4'-dimethyl-diphenylmethane-α,α'-diyl; |
| 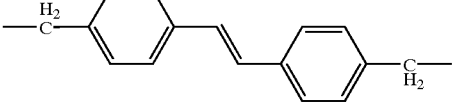 | 4,4'-dimethyl-cis/trans-stilbene-α,α'-diyl; |

| Spacing Group | Name |
|---|---|
| 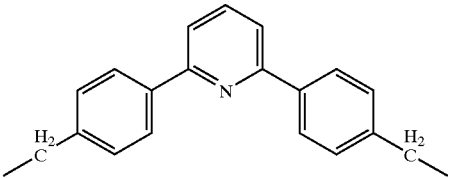 | 2,6-bis(4'-methyl-phenyl)pyridine-α,α'-diyl; |
| 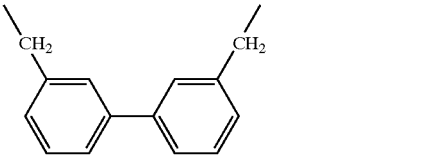 | 3,3'-dimethyl-biphenyl-α,α'-diyl; |
| 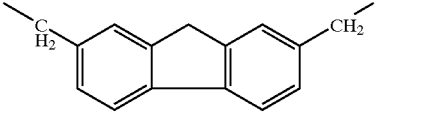 | 2,7-dimethyl-9H-fluorene-α,α'-diyl; |

In the context of this invention halogen represents a fluorine, a chlorine, a bromine or an iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butynyl; 1-, 2-, 3-, 4-pentynyl, or 1,3-pentynyl; 1-, 2-, 3-, 4-, or 5-henynyl, or 1,3-hexynyl or 1,3,5-hexynyl; 1-, 2-, 3-, 4-, 5- or 6-heptynyl, or 1,3-heptynyl, or 1,3,5-heptynyl; 1-, 2-, 3-, 4-, 5-, 6- or 7-octynyl, or 1,3-octynyl, or 1,3,5-octynyl, or 1,3,5,7-octynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkoxy group designates an "alkyl-O-" group, wherein alkyl is as defined above.

In the context of this invention an alkoxy-alkyl group designates an "alkyl-O-alkyl-" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention an amido group designates a substituent of the formula R'—CO—NH— or R'—CO—N(alkyl)-, wherein R' represents hydrogen or an alkyl group as defined above. Examples of preferred amido groups include formamido, acetamido, and propionamido.

In the context of this invention a mono- or poly-cyclic carbocyclic group designates a mono- or polycyclic hydrocarbon group, which group may in particular be an aromatic hydrocarbon group, i.e. a mono- or polycyclic aryl group, or a saturated hydrocarbon group, or a partially saturated hydrocarbon group. Preferred poly-carbocyclic group are the bicyclic carbocyclic groups.

In the context of this invention a mono- or polycyclic aryl group designates a monocyclic or polycyclic aromatic hydrocarbon group. Examples of preferred aryl groups of the invention include phenyl, naphthyl, indenyl, azulenyl, anthracenyl, and fluorenyl.

Examples of saturated and partially saturated hydrocarbon groups include hydrocarbons like cyclopropyl, cyclobutyl, cyclopentyl, cyclohexyl, cycloheptan, and cyclooctan, and bicyclic carbocyclic groups like norbonane and adamantane.

In the context of this invention an aralkyl group designates a mono- or polycyclic aryl group as defined above, which aryl group is attached to an alkyl group as also defined above. Examples of preferred aralkyl groups of the invention include benzyl, and phenethyl.

In the context of this invention a mono- or poly-cyclic heterocyclic group is a mono- or polycyclic group, which group holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6 membered heterocyclic monocyclic groups. Preferred poly-heterocyclic groups of the invention are the bicyclic heterocyclic groups.

Examples of preferred aromatic heterocyclic 5-membered monocyclic groups of the invention include
  furan, in particular 2- or 3-furanyl;
  thiophene, in particular 2- or 3-thienyl;
  pyrrole, in particular 1-, 2- or 3-pyrrolyl;
  oxazole, in particular oxazol-(2-,4- or 5-)yl;
  thiazole, in particular thiazol-(2-,4-, or 5-)yl;
  imidazole, in particular imidazol-(1-,2-,4- or 5-)yl;
  pyrazole, in particular pyrazol-(1-,3-,4- or 5-)yl;
  isoxazole, in particular isoxazol-(3-,4- or 5-)yl;
  isothiazole, in particular isothiazol-(3-,4- or 5-)yl;
  1,2,3-oxadiazole, in particular 1,2,3-oxadiazol-(4- or 5-)yl;
  1,2,4-oxadiazole, in particular 1,2,4-oxadiazol-(3- or 5-)yl;
  1,2,5-oxadiazole, in particular 1,2,5-oxadiazol-(3- or 4-)yl;
  1,2,3-triazole, in particular 1,2,3-triazol-(1-,4- or 5-)yl;
  1,2,4-thiadiazole, in particular 1,2,4-thiadiazol-(3- or 5-)yl;
  1,2,5-thiadiazole, in particular 1,2,5-thiadiazol-(3- or 4-)yl; and
  1,3,4-thiadiazole, in particular 1,3,4-thiadiazol-(2- or 5-)yl.

Examples of preferred aromatic heterocyclic 6-membered monocyclic groups of the invention include
  pyridine, in particular pyridin-(2-,3- or 4-)yl;
  pyridazine, in particular pyridazin-(3- or 4-)yl;
  pyrimidine, in particular pyrimidin-(2-,4- or 5-)yl;
  pyrazine, in particular pyrazin-(2-,3-,5- or 6-)yl;
  1,3,5-triazine, in particular 1,3,5-triazin-(2-,4- or 6-)yl; and
  phosphinine, in particular phosphinin-(2-,3- or 4-)yl.

Examples of preferred saturated or partially saturated heterocyclic monocyclic 5-membered groups of the invention include
  2H-pyrrole, in particular 2H-pyrrol-(2- or 3)yl;
  2-pyrroline, in particular 2-pyrrolin-(1-,2- or 3-)yl;
  3-pyrroline, in particular 3-pyrrolin(1-,2- or 3-)yl;
  pyrrolidine, in particular pyrrolidin-(1-,2- or 3-)yl;
  1,3-dioxolan, in particular 1,3-dioxolan-(2- or 4-)yl;
  imidazolidine, in particular imidazolidin-(1-,2-,3-,4- or 5-)yl;
  2-imidazoline, in particular 2-imidazolin-(1-,2-,4- or 5-)yl;
  3-imidazoline, in particular 3-imidazolin-(1-,2-,4- or 5-)yl;
  4-imidazoline, in particular 4-imidazolin-(1-,2-,4- or 5-)yl;
  pyrazolidine, in particular pyrazolidin-(1-,2-,3-,4- or 5-)yl;
  2-pyrazoline, in particular 2-pyrazolin-(1-,3-,4- or 5-)yl; and
  3-pyrazoline, in particular 3-pyrazolin-(1-,3-,4- or 5-)yl.

Examples of preferred saturated or partially saturated heterocyclic monocyclic 6-membered groups of the invention include
  2H-pyrane, in particular 2H-pyran-(2-,3- or 4-)yl;
  4H-pyrane, in particular 4H-pyran-(2-,3- or 4-)yl;
  piperidine, in particular piperidin-(1-,2-,3- or 4-)yl;
  1,4-dioxolane, in particular 1,4-dioxolan-(2- or 3-)yl;
  morpholine, in particular morpholin-(2-,3- or 4-)yl;
  1,4-dithiane, in particular 1,4-dithian-(2- or 3-)yl;
  thiomorpholine, in particular thiomorpholin-(2-,3- or 4-)yl;
  piperazine, in particular piperazin-(1-,2-,3- or 4-)yl;
  1,3,5-trithiane, in particular 1,3,5-trithian-(2-)yl; and
  1,4-oxazine, in particular 1,4-oxazin-(2-)yl.

Examples of preferred aromatic heterocyclic bi-cyclic groups of the invention include
  indolizine, in particular indolizin-(1-,2-,3-,5-,6-,7- or 8)yl;
  indole, in particular indol-(1-,2-,3-,4-,5-,6- or 7) yl;
  isoindole, in particular isoindol-(1-,2-,3-,4-,5-,6- or 7-)yl;
  benzo[b]furan (benzofuran), in particular benzo[b]furan-(2-,3-,4-,5-,6- or 7-) yl;
  benzo[c]furan (isobenzofuran), in particular benzo[c]furan-(1-,3-,4-,5-,6- or 7-)yl;
  benzo[b]thiophene (benzothiophene), in particular benzo[b]thiophen-(2-,3-,4-,5-,6- or 7-)yl;
  benzo[c]thiophene (isobenzothiophene), in particular benzo[c]thiophen-(1-,3-,4-,5-,6- or 7-)yl;
  benzimidazole, in particular benzimidazol-(1-,2,4-,5-,6- or 7-)yl;
  benzthiazole, in particular benzthiazol-(2-,4-,5-,6- or 7-)yl;
  purine, in particular purin-(2-,6- or 8-)yl;
  quinoline, in particular quinolin-(2-,3-,4-,5-,6-,7- or 8-)yl;
  isoquinoline, in particular isoquinolin-(1-,3-,4-,5-,6-,7- or 8-)yl;
  cinnoline, in particular cinnolin-(3-,4-,5-,6-,7- or 8-)yl;
  phthlazine, in particular phthlazin-(1-,4-,5-,6-,7- or 8-)yl;
  quinazoline, in particular quinazolin-(2-,4-,5-,6-,7- or 8-)yl;
  quinoxaline, in particular quinoxalin-(2-,3-,5-,6-,7- or 8-)yl;
  1,8-naphthyridine, in particular 1,8-naphthyridin-(2-,3-,4-,5-,6- or 7-)yl; and
  pteridine, in particular pteridin-(2-,4-,6- or 7-)yl.

Examples of preferred aromatic heterocyclic tri-cyclic groups of the invention include
  carbazole, in particular carbazol-(1-,2-,3-,4-,5-,6-,7-,8- or 9-)yl;
  acridine, in particular acridin-(1-,2-,3-,4-,5-,6-,7-,8- or 9-)yl;
  phenazine, in particular phenazin-(1-,2-,3-,4-,6-,7-,8- or 9-)yl;
  phenothiazine, in particular phenothiazin-(1-,2-,3-,4-,6-,7-,8-,9- or 10-)yl; and
  phenoxazine, in particular phenoxazin-(1-,2-,3-,4-,6-,7-,8-9- or 10-)yl.

Examples of preferred saturated or partially saturated heterocyclic bi-cyclic groups of the invention include
  indoline, in particular indolin-(1-,2-,3-,4-,5-,6- or 7-)yl;
  3H-indole, in particular 3H-indol-(2-,3-,4-,5-,6- or 7-)yl;
  1H-indazole, in particular 1H-indazol-(3-,4-,5-,6- or 7-)yl;
  4H-quinolizine, in particular 4H-quinolizin-(1-,2-,3-,4-6-,7-,8- or 9-)yl;
  quinuclidine, in particular quinuclidin-(2-,3-,4-,5-,6-,7- or 8-)yl;
  isoquinuclidine, in particular isoquinuclidin-(1-,2-,3-,4-,5-,6-,7- or 8-)yl;
  tropane, in particular tropan-(1-,2-,3-,4-,5-,6-,7- or 8-)yl; and
  notropane, in particular nortropan-(1-,2-,3-,4-,5-,6- or 7-)yl.

In the context of this invention a hetero-alkyl group designates a mono- or poly-cyclic heterocyclic group as described above, which heterocyclic group is attached to an alkyl group as also defined above. Examples of preferred hetero-alkyl groups of the invention include furfuryl and picolyl.

Also, in the context of this invention, a chemical compound comprising a tertiary amino group may also be made quaternary (quaternized) using an alkylation agent, in particular an alkyl halide, preferably the chloride, bromide or iodide of methyl or ethyl.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The chemical compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The chemical compounds of the invention have been subjected to in vitro experiments and found particularly useful as potassium channel blocking agents. More particularly the compound of the invention are capable of selectively blockade of SK channels, e.g. SK1, SK2 and/or SK3 channels.

The compounds tested all showed a biological activity determined as $IC_{50}$ in the sub-micromolar and low micromolar range, i.e. of from below 1 to above 10 $\mu$M. Preferred compounds of the invention show a biological activity determined as described herein in the in the sub-micromolar and micromolar range, i.e. of from below 1 to about 100 $\mu$M.

Therefore, in another aspect, the invention relates to the use of a chemical compound of the invention for the manufacture of medicaments, which medicament may be useful for the treatment or alleviation of a disease or a disorder associated with the activity of potassium channels, in particular SK channels.

In a more preferred embodiment, the chemical compound of the invention may be use for the manufacture of medicaments for the treatment or alleviation of diseases or conditions like respiratory diseases such as asthma, cystic fibrosis, chronic obstructive pulmonary disease and rhinorrhea. convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

Pharmaceutical Compositions

In yet another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the chemical compound of the invention, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 $\mu$g/kg/day i.v., and from about 1 $\mu$g/kg to about 100 $\mu$g/kg/day p.o.

Methods of Therapy

In another aspect the invention provides a method for the prevention, treatment or alleviation of a disease or a disorder or a condition of a living animal body, including a human, which disease, disorder or condition is responsive to blockade of the potassium channel, in particular the SK channel, and which method comprises comprising administering to such a living animal body, including a human, in need thereof a therapeutically-effective amount of a compound of the invention.

The in a preferred embodiment of the method of the invention, the disease or disorder is asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples which are not intended to be in any way limiting to the scope of the invention as claimed.

Example 1

Preparatory Example

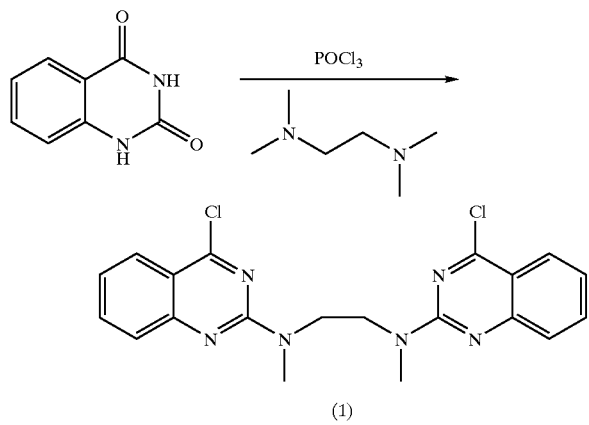

N,N'-bis(4-chloroquinoxalin-2-yl)-N,N'-dimethylethylenediamine (Compound 1)

A suspension of benzoyleneurea (5.0 g; 30.8 mmol) in phosphoroxychloride (70 ml) was stirred under $N_2$ and N,N,N,N-tetramethylethylendiamine (16.33 ml; 108 mmol) was added. The mixture was heated to reflux overnight. The cooled mixture was filtered and the precipitate was washed with dichloromethane. The combined filtrate and washings was concentrated under reduced pressure. Aqueous sodium hydroxide (1 M) was carefully added to the concentrate and the resulting suspension was extracted with dichloromethane. This extract was dried over magnesium sulphate, concentrated under reduced pressure and eluted through silica gel with a mixture of ethyl acetate and ligroin (1:4 v/v) to yield Compound 1 (0.65 g, 5%).

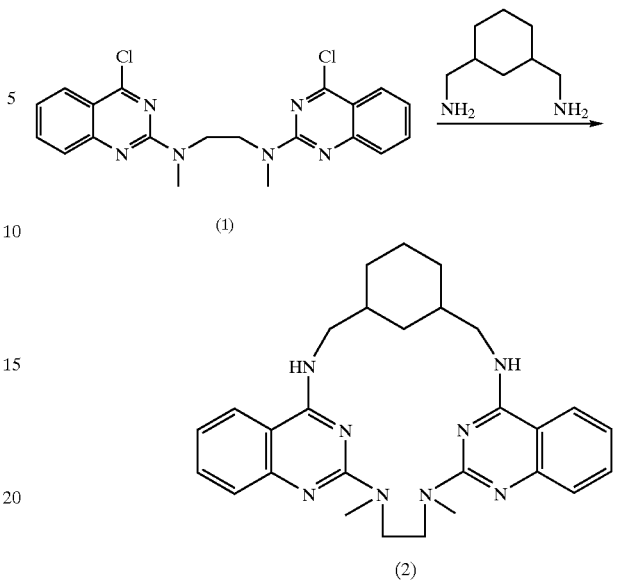

20,23-dimethyl-2,10,18,20,23,25,32,33-octaazahexacyclo[22.7.1.1$^{4,8}$.1$^{11,19}$.0$^{12,17}$.0$^{26,31}$] tetratriaconta-1(32).11,13,15,17,19(33),24,26,28,30-decaene (Compound 2)

To a solution of 1,3-cyclohexanebis(methylamine) (0.2 ml; 1.35 mmol) in anhydrous DMF (70 ml) was added N,N'-bis(4-chloroquinoxalin-2-yl)-N,N'-dimethylethylenediamine (Compound 1; 0.56 g; 1.35 mmol) and the mixture was stirred at 100° C. for ten days. The solvent was distilled off at reduced pressure and the residue was triturated with water to leave the crystalline crude product, which was purified by column-chromatography on silica gel using a mixture of dichloromethane, methanol and aqueous ammonia (90:10:1 v/v/v) as the eluent. Yield of Compound 2: 0.1 g (15%). M.p. 284–285° C.

Example 2

Biological Activity

This example demonstrates the biological activity of a compound (Compound 2) of the invention.

In this experiment. small-conductance $Ca^{2+}$-activated $K^+$ channels (SK channels, isoform 2) cloned from a rat cDNA library were stably expressed in HEK293 cells using standard procedures. The ionic current through the channels was recorded in the whole-cell mode of the patch-clamp technique.

Cells plated on coverstips are placed in a 15 $\mu$l perfusion chamber (flowrate ~1 ml/min), mounted on a IMT-2 microscope equipped with Nomarski or Hoffmann optics. The microscopes are placed on vibration-free tables in grounded Faraday cages.

All experiments are performed at room temperature (20–22° C.). EPC-9 patch-clamp amplifiers (HEKA-electronics, Lambrect, Germany) are connected to Macintosh computers via ITC16 interfaces. Data are stored directly on the harddisk and analysed by the IGOR software according to the manufacturer's instructions.

The whole-cell configuration of the patch clamp technique is applied. Shortly described, the tip of a borosilicate pipette (resistance 2–4 M$\Omega$) is gently (remote control system) placed on the cell membrane. Light suction results in a giga seal (pipette resistance increases to more than 1 G$\Omega$), and the cell membrane is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size), and the series resistance is in the range 3 to 6 MΩ. Rs-as well as capacitance compensation are updated during the experiments (before each stimulus). All experiments with drifting Rs-values are discharged. Leak-subtractions are not performed.

Solutions

The extracellular (bath) solution contains (concentration in mM): 144 KCl, 2 $CaCl_2$, 1 $MgCl_2$, 10 HEPES (pH=7.4).

Test compounds are dissolved as 1000 times concentrated stock solutions in DMSO, and then diluted in the extracellular solution.

In the experiments where the effect of channel activators is quantified (test 475), the intracellular (pipette) solution has the following composition (concentration in mM):

144 KCl, 10 EDTA, 1.4 $MgCl_2$, 5.17 $CaCl_2$, and 10 HEPES (pH=7.2).

The calculated free concentration of $Ca^{2+}$ in this solution is 100 nM, and that of $Mg^{2+}$ is 1 mM. In these experiments, the concentration of $CaCl_2$ is 7.6 mM and that of $MgCl_2$ is 1.2 mM to give calculated free concentrations of 300 nM and 1 mM, respectively.

Quantification

After establishment of the whole-cell configuration, voltage-ramps (usually −100 to +100 mV) are applied to the cell every 5 sec. A stable baseline current is obtained within a period of 100–300 seconds and compounds are then added by changing to an extracellular solution containing the compound to be tested. Very little endogene current (<200 pA at 100 mV compared to 2–20 nA SK current) are activated under these circumstances in native HEK293 cells.

An $IC_{50}$ value is calculated from the kinetics of the block. The time-course of the decrease in current is fitted to the following equation:

$$I=I_0*(1-(C/C+(K_{off}/K_{on})))*(1-\exp(-(C*K_{on}+K_{off})*t)))$$

where
$K_{off}$=off-rate in $s^{-1}$
$K_{on}$=on-rate in $M^{-1}s^{-1}$
$I_0$=basal current in nA
C=drug concentration in μM
$IC_{50}$ equals the ratio $K_{off}/K_{on}$.

In this test Compound 2 of the invention showed a biological activity determined as $IC_{50}$ in the sub-micromolar range, i.e. below 1 μM.

What is claimed is:

1. A compound of Formula II,

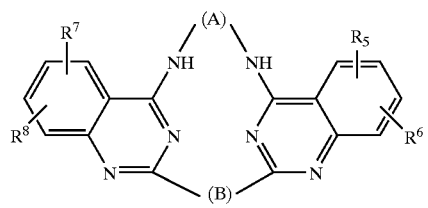

(II)

wherein
A represents a linking group selected from the group consisting of (cis or trans)-1,5-cyclooctylene; (cis or trans)-1,3-dimethylcyclohexane-α,α'-diyl; para-xylene-α,α'-diyl; meta-xylene-α,α'-diyl; 1,3-phenylene; biphenyl-3,3'-diyl; 4,4'-dimethyl-bibenzyl-α,α'-diyl; 4,4'-dimethyl-diphenylmethane-α,α'-diyl; 4,4'-dimethyl-cis/tran-stilbene-α,α'-diyl; 2,6-bis(4'-methyl-phenyl)pyridine-α,α'-diyl; 3,3'-dimethyl-biphenyl-α,α'-diyl; and 2,7-dimethyl-9H-fluorene-α,α'-diyl; and B represents a linking group selected from the group consisting of: N,N'-dimethyl-diamino-methylene; N,N'-dimethyl-diamino-dimethylene and N,N'-dimethyl-diamino-trimethylene; and $R^5$, $R^6$, $R^7$ and $R^8$, independently of each another, represent hydrogen, halogen, trihalogenmethyl, alkyl, alkynyl, amino, nitro, or cyano.

2. The compound of the formula

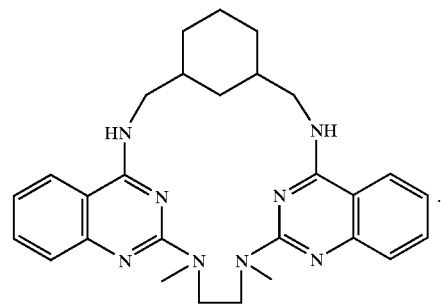

3. A pharmaceutical composition comprising a therapeutically-effective amount of a chemical compound according to claim 1, or a pharmaceutically-acceptable addition salt thereof, together with at least one pharmaceutically-acceptable carrier or diluent.

4. A compound of Formula II,

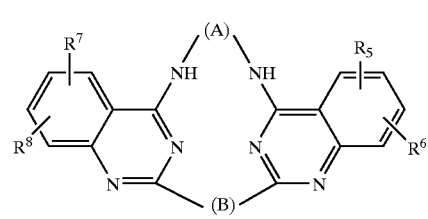

(II)

wherein
A is a di-radical of the formula —$(CH_2)_a$—D—$(CH_2)_b$—, wherein a and b, which may be identical or different, represent the number 0, 1, 2, 3, 4 or 5, and D represents a cycloalkyl group, or an aryl group of from 6 to 12 carbon atoms; and B represents a linking group selected from the group consisting of: N,N'-dimethyl-diamino-methylene; N,N'-dimethyl-diamino-dimethylene and N,N'-dimethyl-diamino-trimethylene; and $R^5$, $R^6$, $R^7$ and $R^8$, independently of each another, represent hydrogen, halogen, trihalogenmethyl, alkyl, amino, nitro, or cyano.

* * * * *